(12) United States Patent
Berthier et al.

(10) Patent No.: US 8,466,232 B2
(45) Date of Patent: Jun. 18, 2013

(54) BIODEGRADABLE GRAFTED COPOLYMERS

(75) Inventors: Damien Berthier, Geneva (CH);
Lahoussine Ouali, Vetraz-Monthoux (FR)

(73) Assignee: Firmenich SA, Geneva (CH)

( * ) Notice: Subject to any disclaimer, the term of this patent is extended or adjusted under 35 U.S.C. 154(b) by 1670 days.

(21) Appl. No.: 11/554,096

(22) Filed: Oct. 30, 2006

(65) Prior Publication Data

US 2007/0054816 A1 Mar. 8, 2007

Related U.S. Application Data

(63) Continuation of application No. PCT/IB2005/001179, filed on May 2, 2005.

(30) Foreign Application Priority Data

May 5, 2004 (EP) .................................... 04101930

(51) Int. Cl.
*C08F 251/00* (2006.01)
*A61Q 13/00* (2006.01)
*A61K 8/91* (2006.01)
*A61K 47/36* (2006.01)

(52) U.S. Cl.
USPC ........................... 525/54.3; 525/410; 525/415

(58) Field of Classification Search
USPC .......................... 510/101; 525/54.3, 410, 415
See application file for complete search history.

(56) References Cited

U.S. PATENT DOCUMENTS

| 5,221,534 A | 6/1993 | Des Lauriers et al. ..... 424/78.03 |
| 5,756,082 A | 5/1998 | Cashin et al. .............. 424/78.03 |
| 2002/0146826 A1 | 10/2002 | Domb .......................... 435/455 |

FOREIGN PATENT DOCUMENTS

| WO | WO 01/79315 A1 | 10/2001 |
| WO | WO 02/39979 A1 | 5/2002 |
| WO | WO 03/105786 A2 | 12/2003 |

OTHER PUBLICATIONS

Ouchi t et al., XP004428343 "Modification of Polylactide Upon Physical Properties by Solution-Cast Blends From Polylactide and Polylactide-Grafted Dextran" Polymer, vol. 44, No. 14, pp. 3927-3933, (2003).
Hedrick J. L. et al., XP000788833, "Dendrimer-Like Star Block and Amphiphilic Copolymers by Combination of Ring Opening and Atom Transfer Radical Polymerization" Macromolecules, , vol. 31, No. 25, pp. 8691-8705, (1998).

*Primary Examiner* — Jeffrey Mullis
(74) *Attorney, Agent, or Firm* — Winston & Strawn LLP (57) ABSTRACT

The invention concerns a biodegradable copolymer composition of a polysaccharide backbone grafted with amphiphilic diblock copolymers, as well as a process for the preparation of such composition and a particle suitable for the release of active ingredients made of such a composition.

11 Claims, 2 Drawing Sheets

FIG. 1

FIG. 2

BIODEGRADABLE GRAFTED COPOLYMERS

CROSS-REFERENCE TO RELATED APPLICATIONS

This application is a continuation of International application PCT/IB2005/001179 filed May 2, 2005, the entire content of which is expressly incorporated herein by reference thereto.

TECHNICAL FIELD

The present invention relates to the field of biodegradable copolymers. It concerns more particularly a novel copolymer composition based on a polysaccharide backbone grafted with amphiphilic diblock copolymers. The compositions of the invention can find use in various fields of application in particular in pharmaceutical, perfume and flavour areas, as they adopt, in a particular environment, a core-shell conformation which renders them suitable to be used as delivery systems for active ingredients. The invention also concerns a process for the preparation of such copolymer compositions.

BACKGROUND ART

Biodegradable copolymer compositions as well as their use as carriers for biologically active materials have been described in the prior art, both in the general literature and in the patent literature. In fact, many biodegradable copolymers have been developed for medical applications, and more particularly for the encapsulation of drugs.

In the patent literature, some disclosures in the area of biodegradable copolymer compositions are directed to the use of diblock, triblock or multiblock copolymers which consist of sequenced structures, wherein segments of various natures (e.g. hydrophobic and hydrophilic segments) are covalently linked together. WO 02/39979, U.S. Pat. No. 5,221,534 or U.S. Pat. No. 5,756,082 provide examples of preparation of such structures and describe their uses as drug delivery systems, as well as in cosmetic compositions or other applications.

On the other hand, by opposition to sequenced structures, grafted structures based on biodegradable polymer compositions have also been the object of patents and patent applications. In particular, systems based on the grafting of single polymers along polysaccharide chains have been disclosed. WO 01/79315 describes for instance copolymer compositions consisting of a hydrophobic macromolecule such as a polylactic acid cross-linked with a water-soluble polymer having multiple hydroxyl functionalities which may serve as potential reaction sites. The described composition can be used as a controlled drug delivery system.

More recently, US patent application 2002/0146826 has described a system based on a polysaccharide chain which has been grafted with an oligoamine on the one hand, and by at least one further group selected from the group consisting of a hydrophobic and an amphiphilic group. The oligoamines are conjugated with at least one oligomer per five saccharide units, whereas the hydrophobic and amphiphilic groups are positioned with at least one group per 50 saccharide units. The document discloses the application of the systems to gene therapy.

SUMMARY OF THE INVENTION

Now, the present invention concerns new biodegradable polymeric systems, based on the use of a polysaccharide backbone which has been grafted with amphiphilic diblock copolymers. Such systems have never been described in the prior art and they proved to constitute very advantageous delivery systems for drugs, flavours, fragrances or other active ingredients.

A first object of the present invention relates to a copolymer comprising a polysaccharide backbone and amphiphilic diblock copolymers grafted on the polysaccharide backbone, each amphiphilic diblock comprising:

a) a hydrophobic polymeric segment directly grafted on the polysaccharide backbone and comprising from 5 to 200 repeated units; and b) a hydrophilic polymeric segment covalently bonded to the hydrophobic segment and comprising from 5 to 300 repeated units.

The compositions proved to adopt a core-shell structure when put into an aqueous medium, and thus form particles that can be useful as delivery systems for active ingredients as varied as drugs, flavours or fragrance ingredients or compositions. These particles, as well as their use as delivery systems and functional compositions such as perfumes, foods or pharmaceutical compositions comprising these delivery systems, are also object of the invention.

Furthermore the present invention concerns a process for the preparation of a copolymer as defined above, which comprises the major steps of preparing a micro-initiator by chemical modification of a polysaccharide; using the macro-initiator to polymerise hydrophobic monomers providing hydrophobic primary segments grafted on the polysaccharide; using the obtained polymer as a micro-initiator to polymerise monomers constituting secondary segments covalently linked to the hydrophobic primary ones; and optionally chemically modifying the secondary segments.

The present invention thus relates to a copolymer comprising a polysaccharide backbone and amphiphilic diblock copolymers grafted on the polysaccharide backbone.

In a preferred embodiment, the amphiphilic diblock copolymers are grafted on the backbone with a degree of substitution via hydroxyl functions comprised between 30% and 80%. Each amphiphilic diblock comprises a hydrophobic polymeric segment directly grafted on the polysaccharide backbone, comprising from 5 to 200 repeated units, and a hydrophilic polymeric segment covalently bonded to the hydrophobic segment comprising from 5 to 300 repeated units. In a preferred embodiment of the invention, the hydrophobic segments comprises 15-100 repeated units, and the hydrophilic polymeric segment comprises 15-200 repeated units.

Preferably, each amphiphilic diblock consists of a hydrophobic polymeric segment and a hydrophilic polymeric segment.

The copolymer of the invention is novel, as no document from the prior art has ever described the grafting of a polysaccharide with amphiphilic diblock copolymers. The composition of the invention, besides being novel, proved to form particles which can be very useful as delivery systems for active ingredients enclosed therein. In fact, in an aqueous medium, the amphiphilic copolymers of the invention adopt a core-shell structure, the physico-chemical characteristics of which can be tuned by varying the degree of polymerisation of each segment, the functionality of the amphiphilic block and the grafting density. Depending on the latest parameter, the copolymer compositions can form a stable aqueous dispersion of isolated macromolecules.

More objects, aspects and advantages of the invention will become apparent from the detailed description hereinafter.

DETAILED DESCRIPTION OF THE PREFERRED EMBODIMENTS

The biodegradable polymer of the invention is based on a polysaccharide backbone which has been grafted with amphiphilic diblock copolymers, preferably with a degree of substitution via hydroxyl functions comprised between 30% and 80%. Any polysaccharide, preferably biodegradable, can suit the invention. Typical examples of appropriate polysaccharide chains include those selected from the group consisting of dextrans, arabinogalactan, pullulan, cellulose, cellobios, inulin, chitosan, alginates, hyaluronic acid and cyclodextrins. According to a preferred embodiment, the polysaccharide used in the present invention has a molecular weight higher than 800 g/mol.

Preferably, the copolymer of the invention is a biodegradable copolymer.

Preferably, the copolymer of the invention is present in the form of a copolymer composition.

The amphiphilic diblock copolymers grafted on the polysaccharide backbone consist each of a hydrophobic polymeric segment comprising from 5 to 200, preferably 15-100 repeated units the hydrophobic polymeric segment being directly grafted on the polysaccharide; and a hydrophilic polymeric segment comprising from 5-300, preferably 15 to 200 repeated units, which is covalently bonded to the hydrophobic segment.

Hydrophobicity and hydrophilicity of the segments constituting the amphiphilic diblock copolymer entity is defined as follows: A polymer segment is hydrophobic if it is either insoluble in water or less soluble in water than the hydrophilic polymer segment. A polymer segment is hydrophilic if it can be dissolved at 0.01 wt. % or more in water at room temperature (25° C.) following the procedure of U.S. Pat. No. 6,733, 787, Example 2, which is incorporated herein by reference. For example, a diblock-copolymer ([A]n-[B]p) grafted on a polysaccharide backbone fulfils the hydrophobicity/-philicity requirements of the present invention if a polymer [A]n cannot be dissolved at 0.01 wt.-% in water and if a polymer [B]p, in contrast, can be dissolved at 0.01 wt.-%. in water.

As a generally good indication, the calculated Van Krevelen solubility parameter, can be adduced for determining if a segment of the copolymer of the invention is hydrophobic or hydrophilic: Van Krevelen/Hofzyger "Properties of Polymers", p. 200-225 by D. W. van Krevelen (Elsevier, 1990). A polymer block or segment is hydrophobic if the vanKrevelen/ Hofzyger solubility parameter and 3-D solubility parameter is <25. The polymer is hydrophilic if the parameter is ≧25.

For determining the parameter values for the purpose of the present invention, a number of 8 polymerised monomeric units with unrepeated terminal endings replaced by H— are taken as a reference molecule. For example, for a polymer comprising tert-butyl acrylate as monomeric moieties the standard-molecule below is used to calculate the vanKrevelen/Hofzyger solubility parameter.

The vanKrevelen/Hofzyger solubility parameter can be approximated by software tools like Molecular Modeling Pro, version 5.22, commercialized by Norgwyn Montgomery Software Inc, ©2003. For the polymer above, a value of 29.35 is obtained.

Alternatively, Hydrophobicity and hydrophilicity can be defined using the Hildebrand solubility parameter, also called Hansen solubility parameter, well known in the art, which characterises the polarity of chemical ingredients. Ethanol is usually taken as reference, the latter having a solubility parameter δ of 25. A segment will thus be considered as hydrophobic when its Hansen solubility parameter is below or equal to 25 and as hydrophilic when its solubility parameter is above 25. The Hansen solubility parameter may be approximated, by the above indicated software and standard-molecule.

Hydrophobic polymeric segments susceptible of being grafted directly onto the polysaccharide backbone are characterised by the number of repeated units which is comprised between 5 and 200, preferably 15 and 100. They are preferably selected from the group consisting of polylactides, polycaprolactone, polypropylene glycol and polyanhydrides.

Hydrophilic polymeric segments susceptible of being covalently bonded to the hydrophobic polymeric segments are characterised by the number of repeated units which is comprised between 5 and 300, preferably 15 and 200. They are preferably selected from the group consisting of poly (meth)acrylic acid, polydimethyl aminoethyl(meth)acrylate, polytrimethyl ammonium ethyl(meth)acrylate salts, polyhydroxyethyl(meth)acrylate, polymethylether diethyleneglycol (meth)acrylate, polyethylene oxide, polyvinylpyrrolidone, polyaminoacids and polyacrylonitriles. The term (meth)acrylate encompasses the corresponding acrylates and/or methacrylates.

In an aqueous environment the copolymer composition of the invention takes the organised form of a core-shell. Therefore, another object of the invention concerns a particle having a core-shell structure, consisting of a biodegradable copolymer composition as defined above. More particularly, when contacted with an aqueous medium, the hydrophobic blocks of the composition according to this invention are grouped so as to constitute the core and the hydrophilic blocks are arranged so as to form a shell around the hydrophobic block. The system is arranged around the polysaccharide backbone forming a particle and it can thus be advantageously used as a delivery system for an active ingredient, in particular for a hydrophobic ingredient that would be, due to its nature, embedded in the core part, the polymer matrix thus providing a controlled delivery system for this active ingredient.

The above-mentioned particles are obtainable by a process comprising contacting the copolymer composition of the invention with an aqueous medium.

They have a mean diameter preferably comprised between 10 and 500 nm.

The particles thus formed are susceptible of entrapping an active ingredient such as a drug, a flavour or a fragrance ingredient or composition and can be used as delivery systems for the controlled release of the latter ingredient or composition through its diffusion from the copolymer composition, prior to copolymer degradation, or by release from the copolymer matrix as the polymer degrades. The release of encapsulated active ingredients may be regulated in part by the molecular weight of the various polymers of the composition and also by the grafting density.

In a particular embodiment, the active material susceptible of being protected is a perfume or flavour ingredient or composition. The terms "perfume or flavour ingredient or composition" are deemed to designate a variety of flavour and fragrance materials of both natural and synthetic origin. They include single compounds and mixtures. Natural extracts can also be encapsulated within the particles of the invention; these include e.g. citrus extracts, such as lemon, orange, lime, grapefruit, or mandarin oils, or essential oils of spices, amongst other. Specific examples of such flavour and perfume components may be found in the current literature, e.g. in Perfume and Flavour Chemicals, 1969, by S. Arctander, Montclair N.J. (USA); Fenaroli's Handbook of Flavour Ingredients, CRC Press or Synthetic Food Adjuncts by M. B. Jacobs, van Nostrand Co., Inc. They are well known to the skilled person in the art of perfuming, flavouring and/or aromatising consumer products, i.e. of imparting an odour or taste to a consumer product.

The active ingredient can be loaded into the particles by absorption and, or diffusion. This loading can be obtained by dispersing a pre-mixed composition of copolymer and active ingredient into an aqueous medium. More particularly, a process for the preparation of a delivery system according to the invention comprises the steps of preparing a copolymer composition as detailed below, drying the composition and mixing the dried composition with an active ingredient or composition. The latter can be present in the system in amounts varying between 5 and 70% by weight relative to the total weight of the delivery system.

When the particles of the invention enclose a perfume ingredient or composition, they can be advantageously used in many applications in perfumery, both in fine and functional perfumery. In particular, they can be used, together with other perfuming ingredients, solvents or adjuvants of current use in the preparation of a perfume formulation, in applications such as in a perfume, an eau de toilette, or an alter-shave lotion, but also in functional products, together with functional constituents of bases present in products such as soaps, bath or shower gels, shampoos or other hair-care products, cosmetic preparations, deodorants or air-fresheners, detergents or fabric softeners or household products. Functional ingredients present in these bases have detergent, cleaning, purifying, softening, antibacterial, or stabilising-type of properties.

In all applications, the particles of the invention filled in with perfume may be used as such or as part of a perfuming formulation comprising other perfuming ingredients, solvents or adjuvants or current use in the preparation of perfume formulations.

The terms "perfume formulation" must be understood within the framework of the art of perfumery. More particularly, they designate in a general manner, a blend of odoriferous materials, perceived as having its own unique and aesthetically appropriate identity. It is a carefully balanced blend (specific ingredients in specific proportions) in which each material plays its part in achieving the overall fragrance. This creative and original composition is thus structurally characterised by a formulation constituted by the ingredients themselves and their relative proportions.

A perfume formulation in the field of perfumery is not just a mixture of pleasantly smelling materials. On the other hand, a chemical reaction involving reactants and products formed, which constitutes a dynamic system, cannot be assimilated, unless otherwise specified, to a perfume formulation, even when odoriferous materials are present among the starting products, the formed products, or even both of them.

Now, apart from having a well defined identity, a perfume or perfume formulation must meet a number of technical requirements. It must be for instance sufficiently strong, it must be diffusive, it must be persistent, and it must retain its essential fragrancing character throughout its period of evaporation.

Besides, a perfume formulation must be adapted as a function of the application for which it is intended. In particular, a perfume formulation may be designated for fine fragrance or designed for a functional product (soap, detergent, cosmetics, etc.) which needs to present a degree of persistence appropriate to the use for which it is intended. The formulations must also be chemically stable in the end product. The technique by which this is achieved is an essential part of the perfumer's art, and it is needed many years of dedicated work to arrive at the level of experience necessary to formulate perfumes or perfume formulations that are not only original but also well made.

Now, these technical considerations imply that a perfume formulation may comprise other ingredients than perfuming materials, which are hereby designated as "solvents or adjuvants of current use in the preparation of a perfume formulation".

First of all, independently of whether the composition is designed for fine perfumery or for use in a technical product, a solvent system is most of the time part of the fragrance. Solvents currently used in the preparation of a perfume formulation include, but are not limited to, dipropylene glycol, diethyl phtalate, isopropyl myristate, benzyl benzoate, 2-(2-ethoxyethoxy)-1-ethanol or ethyl citrate for the most commonly used.

On the other hand, the creation of a perfume formulation intended for a functional product involves considerations both of hedonics (how should the product smell) and of the technique of adapting the perfume to the product formulation or, as is often the, to the product base. The perfume formulation may therefore comprise "adjuvants" which can have many different functions, depending on the base which has to be perfumed. These adjuvants include for instance stabilisers and antioxidants.

Today, the range of product types and product formulations that are perfumed has become so extensive and subjected to such frequent changes that an approach based on a product-by-product basis and on the definition for each case of the adjuvants that can be used, is impractical. That is why the present application does not comprise an exhaustive list or detailed approach of the solvents or adjuvants currently used in perfume formulations. However, a skilled person in the art, i.e. an expert perfumer, is capable of choosing these ingredients as a function of the product to be perfumed and of the nature of the perfuming ingredients in the perfume.

On the other hand, when the particles of the invention enclose a flavour ingredient or composition, they may be added to a flavouring composition or directly to an edible ready-to-consume product. By "flavouring composition", it is meant here a mixture of flavouring ingredients, solvents or adjuvants or current use for the preparation of a flavouring formulation, i.e. a particular mixture of ingredients which is intended to be added to an edible composition to impart, improve or modify its organoleptic properties, in particular its odour, flavour and/or taste.

Solvents and adjuvants of current use for the preparation of a flavouring formulation are also well known in the art. They allow flavouring formulations to meet technical requirements, such as stability or tonality persistence. The solvent is most of the time part of a flavouring composition. Solvents currently used in this framework include for instance benzyl alcohol, propylene glycol, triacetine, vegetable oils, ethanol or limonene. The adjuvants, on the other hand, can have many various functions in a flavouring composition. They include for instance stabilizers.

On the other hand, the particles of the invention can also be directly added to a ready-to-consume or end-product. In other words, they can either be initially added to a flavouring composition as defined above, the resulting composition being then added to an end-product, or be added independently of a flavouring composition to an edible product.

In a third embodiment, when the particles of the invention enclose a drug, they can be added to pharmaceutical compositions.

Other actives may be enclosed in the particles of the invention, such as nutraceuticals, or sweeteners for instance. The cited actives should thus not be considered as limiting the invention.

In compositions such as perfume formulations, flavouring compositions or pharmaceutical compositions, the particles of the invention can be used in a wide range of concentrations, depending on the application and on the desired effect. A skilled person in the art is able to choose the right dosage for a particular application.

Another object of the invention is a process for the preparation of a biodegradable copolymer composition as defined above. The process of the invention comprises the major steps of preparing a micro-initiator by chemical modification of a polysaccharide; using the macro-initiator to polymerise hydrophobic monomers providing hydrophobic primary segments grafted on the polysaccharide; using the obtained polymer as a micro-initiator to polymerise monomers constituting secondary segments covalently linked to the primary segments and if necessary chemically modifying the hydrophilic segments.

More particularly, the first step of the process of the invention consists in partially protecting the hydroxyl groups of a polysaccharide chain by silylation of hydroxyl functions. The ratio between the polysaccharide hydroxyl functions and the sylilation agent is comprised between 1 and 3 equivalents so as to provide 20 to 70% of protected polysaccharide hydroxyl functions. The ratio of protected hydroxyl functions can be controlled by NMR analysis. Sylilation is well known in the art and a skilled person is able to choose suitable reaction conditions and a suitable sylilation agent. Hexamethyldisilazane is commonly used as sylilation agent. A detailed description of this step will be given in the examples below.

The unprotected hydroxyl functions of the modified polysaccharide are used in the second step of the process as initiator for the polymerisation of hydrophobic monomers. In other words, the obtained modified polysaccharide backbone constitutes a macro-initiator capable of initiating the polymerisation of various monomers, which polymerisation is carried out in the second step of the process by ring opening polymerisation. During this second step, hydrophobic segments also referred to as "primary segments" are thus grafted onto the polysaccharide backbone. Preferably, the polymerisation is carried out at a temperature comprised between 120 and 150° C. and in the presence of a catalyst. Specific experimental conditions will be given in a more detailed manner in the examples below.

In a third step, the ending groups of the hydrophobic segments now grafted on the polyaccharide backbone are esterified by means of an initiator, namely an alkyl bromide, in order to provide bromide functions. This newly formed macro-initiator is capable of polymerising monomers, such as (meth-) acrylate monomers, which polymerisation constitutes the last essential step of the process. In a particular embodiment, this polymerisation is carried out by Atom Transfer Radical Polymerization (ATPR), which is a known technique commonly used for the synthesis of well-defined diblock, triblock and grafted copolymers, as reported in reference articles, such as in Hedrick J. L. et al., Macromolecules, 1998, 31, 8691. This article describes that the esterification of hydroxyl functions of a hydrophobic block can be obtained by an initiator such as an alkyl bromide. This process allows the polymerisation of a wide range of functional monomers and is not sensitive to protonic solvents or functions such as hydroxyl. During the fourth step of the process according to the invention, monomers are polymerised to provide secondary segments which are covalently bonded to the primary hydrophobic segments. In a first embodiment, the monomers used in this step are hydrophilic and this step this directly lead to the desired product, namely amphiphilic polymer diblocks grafted on a polysaccharide chain. Now, according to a second embodiment, the monomers polymerised in the fourth step of the process are hydrophobic. In that case, a fifth step is necessary to modify the secondary segments in order to render them hydrophilic. This is possible through a chemical modification of the latter segment. Therefore, functions present on the secondary segments can be chemically modified in a last step of the process. As example, quaternization can be performed in order to provide a cationic shell of the comb. Hydrolysis is another possibility of chemical modification. These modifications can also influence the solubility of the particles in water.

The described process allows to provide a composition which takes a core-shell structure when contacted with water. The latter has a hydrophilic shell, which can be anionic (e.g. with polymethacrylic acid), cationic (e.g. with salt of polytrimethyl ammoniumethyl methacrylate) or non-ionic (e.g. with polyhydroxyethyl methacrylate, polymethylether diethyleneglycol methacrylate).

The present invention further relates to a perfumed product comprising the copolymer of the present invention. Preferably, the perfumed product is a liquid product.

For example, the perfumed product is a perfume, an eau de toilette, a shampoo, a conditioner, a shower gel, a soap (liquid or solid), a cream, a lotion, a liquid detergent, a solid detergent, or a fabric softener. The polymer of the invention may be directly added to the product, if it is a liquid. Alternatively, it first be brought in contact with a perfume in order to absorb or associate fragrance compounds within its hydrophobic block. Thereafter, the polymer may be added to the product at any stage in the manufacturing of the product, preferably when perfumes are added.

Figure 1:
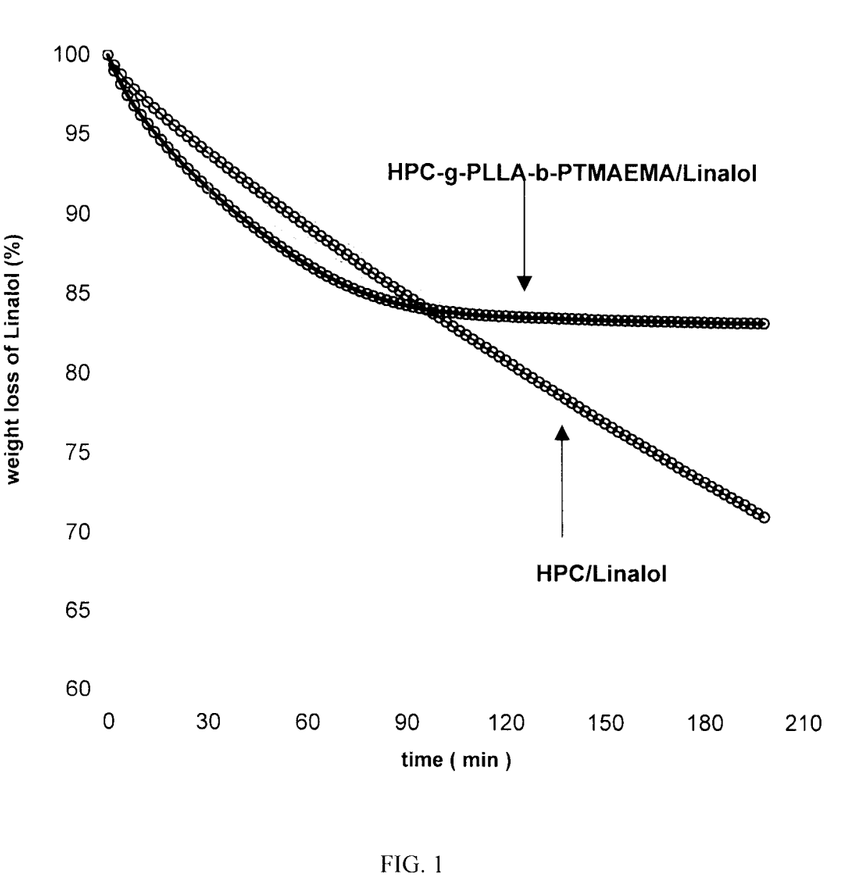
FIG. 1 represents isotherm curves obtained at 25° C. for hydroxypropyl-cellulose/linalool samples on the one hand and HPC-g-PLLA-b-polytrimethylammonium ethyl methacrylate salt (PTMAEMA)/linalool samples on the other hand.

FIG. 1 shows the corresponding average curves showing the evolution of the weight loss of linalool with time. One could observe a significant effect of the copolymer on the fragrance release. The isotherm of the release of linalool seems to be composed of two regimes: a fast regime at the beginning of the isotherm followed by a slow one. This effect is not observed for the HPC samples.

Figure 2:
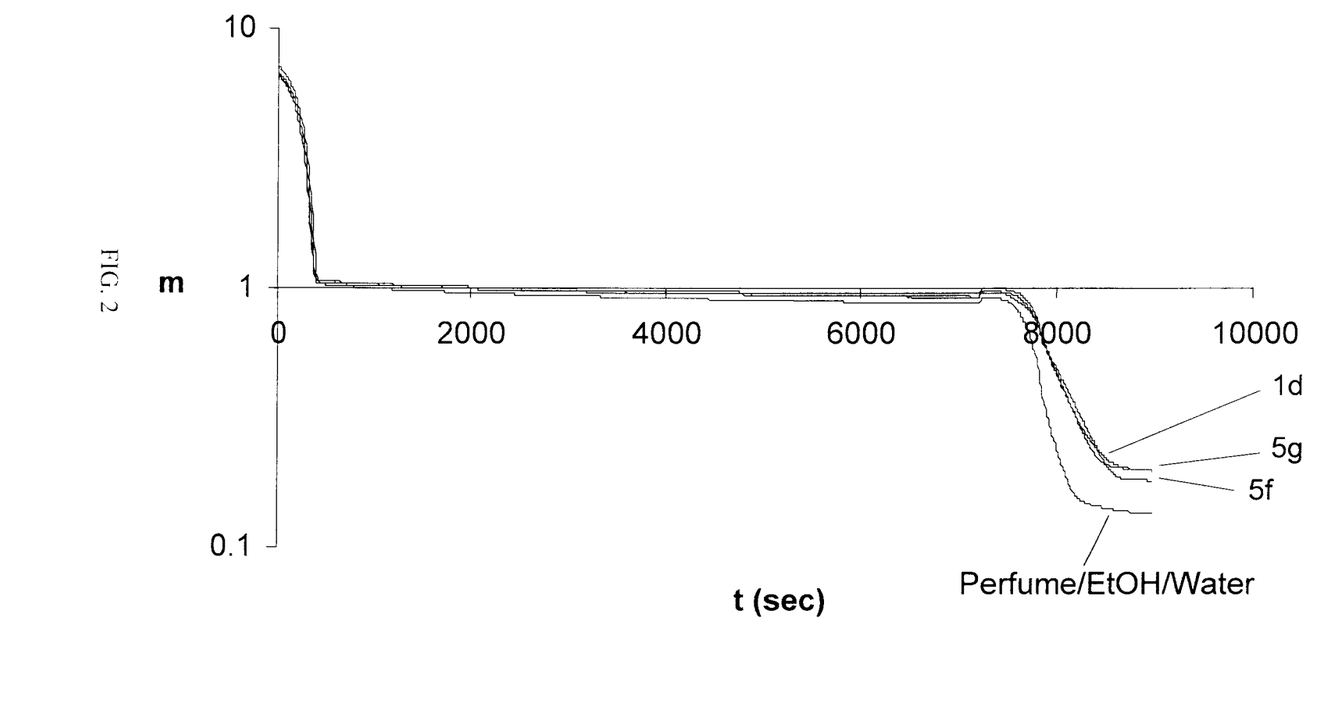
FIG. 2 represents the weight loss of an Eau de toilette (EDT) in the presence (5f, 5g, 1d) or not (Perfume, EtOH/ Eau) of grafted polymers of the invention by thermogravimetric analysis over time. The weight loss at 50° C. over 115 minutes forms a plateau, with samples supplied with the polymer of the invention (5f, 5g, 1d) have less perfume loss than the control.

FIG. 2 shows the corresponding average curves showing the evolution of the weight loss of a fragrance with time in EDT, in the presence or not of grafted copolymers. There are three main phases, the first one corresponding to the loss mainly of water and ethanol, the second one is a plateau persisting for about 3000 seconds characterized by low loss of fragrance at 50° C. and the last one, the complete loss of fragrance by gradually increasing the temperature to 150° C.

EXAMPLES

The invention will now be described in a more detailed manner in the following examples wherein the temperatures are indicated in degrees Celsius and the abbreviations have the usual meaning in the art.
Modes of Carrying out the Invention
General Comments
a) Chemicals Solvents and pentamrethyldiethylenetriamine (PMEDETA) were distilled on $CaH_2$ and stored under nitrogen. Methacrylate and acrylate monomers were purified by filtration on a column of an inhibitor-remover (CAS 9003-70-7; origin: Aldrich). The cupper bromide (CAS 7787-70-4 origin: Aldrich) and the hydroxypropyl-cellulose (Mw=100000 g·mol$^{-1}$; origin: Aldrich, CAS 9004-64-2) were used as received. The (3S)-cis-3,6-dimethyl-1,4-dioxane-2,5-dione was recrystallized in ethyl acetate before used.
b) Size Exclusion Chomatography (SEC)

SEC measurements were carried out with a column Macherey-Nagel Nucluogel GPC 104-5. As a solvent, THF HPLC grade was used. The polymer concentration was fixed at 4 mg/ml. The flow rate was 1 ml/min and the injection volume was 50 microliters.

Example 1

Synthesis of a Biodegradable Copolymer Composition According to the Invention—Degree of Substitution of 66%
a) Synthesis of Functionalised Hydroxypropylcellulose with Trimethylsilyl Group (HPC-g-TMS)

In a three-necked round bottom flask of 100 ml, 4 g of HPC (M=$10^5$ g·mol$^{-1}$, n=4.10$^{-5}$ mmol, $DP_n$=150, MU=350.41 g·mol$^{-1}$) were solubilized in 60 ml of dried acetonitrile (distilled and stored on molecular sieve). 2.66 Ml of hexamethyldisilazane (M=161.39 g·mol–1, n=12.77 mmol, m=1.89 g, d=0.7742, m=2.06 g) were added dropwise and the media was heated at 90° for 4 h under nitrogen. The polymer was obtained by precipitation in water (three times) to give a white solid, which was dried under vacuum for 24 h.

m=4.75 g, yield=80%.
Analytical Data:
NMR $^1$H (400 MHz, 25°, CDCl$_3$): 5.00–3.00 (m, 5H, HPC backbone); 1.13 (s broad, 3H, Me HPC); 0.20 (s, 3H, SiMe$_3$).
$^{13}$C (100 MHz, 25°, CDCl$_3$): 102.29(q)-82.82(d)-81.70 (d)-75.10(d)-74.73(d)-73.29(d)-67.79(d)-67.63(d)-68.05 to 64.81(d)-18.56(q)-17.99(q)-17.41(d)-17.34(d)-0.27(d).

IR (cm$^{-1}$): 3478(s)-2965(m)-2932(m)-2896(m)-2871(m)-1638(s)-1451(s)-1406(s)-1372(m)-1315(s)-1248(s)-1083 (m)-1007(m)-928(s)-889(s)-835(s)-747(m).

GPC (THF, standard PMMA): $M_n$=96000 g·mol$^{-1}$; $M_w$=243000 g·mol$^{-1}$; Ip=2.54.
b) Synthesis of Hydroxypropylcellulose Grafted with poly-L-lactic Acid (HPC-g-PLLA)

In a three-necked round bottom flask of 100 ml with a refrigerator, 200 mg of HPC-g-TMS (66% OH group, MU=408.60 g·mol$^{-1}$, n=0.98 mmol) and 7.06 g of L-lactide (M=144.13 g·mol$^{-1}$, n=48.98 mmol) were dried under vacuum for 1 h. These solids were solubilized into 25 ml of dried xylene. The media was warmed up to 135° and one drop of tin octaote was added to initiate the polymerisation. The media was stirred at 135° for 72 h. Then the polymer was precipitated into cold heptane and filtered to give a white solid, which was dried under vacuum. In order to remove all of the monomer, the copolymer was solubilized in acetone and precipitated it in cold water to obtain a white solid.

m=5.92 g, yield=82%.
Analytical Data:
NMR $^1$H (400 MHz, 25°, CDCl$_3$): 5.16 (q, 60H, OC—CH(CH$_3$)—O); 5.0–3.0 (m, 10H, HPC backbone); 4.35 (q, 1H, OC—CH(CH$_3$)—O); 1.58 (d, 180H, OC—CH(CH$_3$)—O); 1.49 (d, 3H, OC—CH(CH$_3$)—O); 1.23 (m, 3H, Me HPC); 1.12 (m, 6H, Me HPC); 0.14 (s, 3H, SiMe$_3$).
$^{13}$C (100 MHz, 25°, CDCl$_3$): 169.62(qu)-69.02(d)-66.71 (d)-20.53(q)-16.66(d).

IR (cm$^{-1}$): 3641 (w)-3509(w)-2996(w)-2945(w)-2881 (w)-1748(s)-1453(m)-1382(m)-1358(m)-1302(w)-1267(w)-1209(m)-1180(s)-1128(s)-1085(s)-1043(s)-956(w)-918(w)-870(m)-754(m)-694(w).

GPC (THF, standard PS): Mn=835000 g·mol$^{-1}$. Mw=1700000 g·mol$^{-1}$, Ip=2.03
c) Synthesis of HPC-g-PLLA-initiator In a three-necked round bottom flask, 5.80 g of HPC-g-PLLA (MU=3290 g·mol$^{-1}$; $n_{OH}$=3.52 mmol) were solubilized into 20 ml of distilled THF. This solution was cooled down to 0°. Then, 740 μL of 2-bromopropionyl bromide (M=215.88 g·mol$^{-1}$, n=7.06 mmol, m=1.52 g) were added, followed by 983 μL of Et$_3$N (M=101.19 g·mol$^{-1}$, n=7.06 mmol, m=713 mg, d=0.7255). The media was stirred at room temperature for 48 h to give a suspension. The polymer was precipitated two times into water to give a solid, which was solubilized in acetone and precipitated into cold heptane. The solid was dried under vacuum for 24 h.

m=5.80 g. yield=92%.
Analytical Data
NMR $^1$H (400 MHz, CDCl$_3$): 5.18 (q, 35H, Br—CH (Me)—CO—O—CH(Me)—CO); 4.42 (m, 1H, O—CH(Me)—CO—O—CH(Me)Br); 5.09–2.60 (m, 5H, HPC backbone); 1.95 (m, 3H, OC—CH(Me)—Br); 1.58 (d, 105H, O—CH(Me)—O); 1.11 (m, Me HPC).
$^{13}$C (100 MHz, CDCl$_3$): 169.62(qu)-69.02(d)-69.46(d)-21.60(q)-16.66(q).

IR (cm$^{-1}$): 3504(w)-2996(w)-2945(w)-2876(w)-2648(w)-1748(s)-1720(w)-1601(w)-1452(m)-1383(m)-1358(m)-1305(w)-1267(w)-1210(m)-1180(s)-1128(s)-1082(s)-1042 (s)-956(w)-918(w)-870(m)-755(m)-694(m).

GPC: (THF, standard PS): Mn=706000 g·mol$^{-1}$, Mw=1684000 g·mol$^{-1}$, Ip=2.39
d) Synthesis of hydroxypropylcellulose-g-poly-L-lactic acid-b-polydimethylamino-ethyl Methacrylate (HPC-g-PLLA-b-PDMAEMA)

In a two-necked round bottom flask of 50 ml, 0.5 g of HPC-g-PLLA-initiator (Mu-3560 g·mol$^{-1}$, n-=0.14 mmol) were solubilized in 7.85 ml of distilled anisole. Then, 4.73 ml of 2-(N,N-dimethylaminoethyl)methacrylate (M=157.21 g·mol$^{-1}$, d=0.933, n=28.09 mmol, DPn=100, m=4.41 g) and 59 μl of HMTETA (M=173.30 g·mol$^{-1}$, d=0.83, n=0.28 mmol) were added and followed by two freeze-pump-thaw cycles. Then, the cupper bromide was added (M=143.45 g·mol$^{-1}$, m=40 mg, n=0.28 mmol) and degassed by one freeze-pump-thaw cycle. The media was warmed up to 60° and stirred for 3 h. The polymerisation was stopped by freezing in liquid nitrogen and the media was diluted in THF. The solution was filtered on a silica gel column and the solvent was removed. The polymer was dissolved in chloroform and precipitated into cold heptane (0°) to give a yellow solid.

m=2.4 g. yield=48%.

Analytical Data:

NMR $^1$H (400 MHz, 25°, CDCl$_3$): 5.15 (q, 1H, Initiator-O—CH(Me)—CO); 5.0–3.0 (HPC backbone); 4.06 (m, 6H, O—$\underline{CH_2}$—CH$_2$—N); 2.57 (m, 6H, CH$_2$—N); 2.30 (s, 18H, N$\underline{Me_2}$); 2.10–1.70 (m, 6H, $\underline{CH_2}$—C-PDMAEMA backbone); 1.59 (m, 3H, O—CH($\underline{Me}$)—CO); 1.15–0.90 ($\underline{Me}$-C-PDMAEMA backbone, 3H).

$^{13}$C (100 MHz, 25°, CDCl$_3$): 178.02(qu)-177.67(qu)-177.31(qu)-176.58(qu)-169.67(qu)-68.96(q)-63.03(t)-62.87(t)-57.06(t)-56.97(t)-54.04(t)-52.11(t)-45.82(q)-44.92(qu)-44.56(qu)-18.41(m)-16.61(m).

IR (cm$^{-1}$): 2943(s)-2861(w)-2818(m)-2766(s)-1758(s)-1722(s)-1453(s)-386(m)-1359(m)-1333(w)-1266(m)-1178(w)-1133(w)-1096(w)-1041(w)-1015(w)-956(m)-848(m)-778(m)-748(m).

GPC (THF, standard PMMA): No data available. Slightly soluble in THF.

e) Synthesis of HPC-g-PLLA-b-PTMASEMA (25-75)

In a two-necked round bottom flask of 50 ml, washed and dried, 1.0 g of HPC-g-PLLA-b-PDMAEMA (Mu=36400 g·mol$^{-1}$, n=0.028 mmol) were solubilized in 10 ml of distilled THF. Then 168 µL of dimethylsulfate (10% in THF) were added dropwise (M=126.13 g·mol$^{-1}$, n=1.94 mmol, d=1.3322, m=225 mg). The media was stirred 12 h at RT. The product precipitated and was obtained by filtration to give a white solid.

m=1.2 g. yield=96%.

Analytical Data:

NMR $^1$H (400 MHz, 25°, MeOD): 5.18 (q, Initiator-O—CH(Me)—CO); 4.45 (m, O—CH$_2$—CH$_2$—N$^+$); 4.15 (m, O—CH$_2$—CH$_2$—N); 3.85 (m, O—CH$_2$—CH$_2$—N$^+$); 3.71 (m, MeSO$_4$$^-$); 3.31 (m, N$^+$Me$_3$); 2.51 (m, 6H, CH$_2$—N); 2.45 (s, 18H, N$\underline{Me_2}$); 1.94 (m, $\underline{CH_2}$—C-PDMAEMA/PTMASEMA backbone); 1.55(m, 3H, O—CH($\underline{Me}$)—CO); 1.30–0.80 ($\underline{Me}$-C-PDMAEMA/PTMASEMA backbone, 3H).

$^{13}$C (100 MHz, 25° C., MeOD): 179.46(qu)-178.39(qu)-70.35(d)-63.44(t)-57.76(t)-55.22(d)-54.50(d)-46.05(qu)-45.72(d)-45.56(d)-20.07(q)-18.30(d)-17.10(q).

IR (cm$^{-1}$): 3429(w)-3033(w)-2987(w)-2943(m)-2861(w)-2820(m)-2768(m)-2653(w)-1756(s)-1721(s)-1454(s)-1385(m)-1360(m)-1219(s)-1179(s)-1141(s)-1086(s)-1057(s)-1006(s)-953(s)-854(w)-740(s).

Example 2

Synthesis of a Biodegradable Copolymer Composition According to the Invention—Polysaccharide Backbone with a Degree of Substitution of 66%

Steps a), b) and c) were carried out as described in Example 1.

d) Synthesis of hydroxypropylcellulose-g-poly-L-lactic acid-b-polytertiobutyl-methacrylate (HPC-g-PLLA-b-P$^t$BuMA) (66% PLLA-b-P$^t$BuMA (40/60))

In a two-necked round bottom flask of 50 ml. 0.50 g of HPC-g-PLLA-initiator (Mu=3560 g·mol$^{-1}$, n=0.14 mmol) were solubilized in 7.50 ml of distilled THF. Then, 4.60 ml of tertio-butylmethacrylate (M=142.20 g·mol$^{-1}$, d=0.875, n=28.09 mmol, DPn=100, m=4.00 g) and 59 µl of PMDETA (M=173.30 g·mol$^{-1}$, d=0.83, n=0.28 mmol) were added and followed by two freeze-pump-thaw cycles. Then, the cupper bromide was added (M=143.45 g·mol$^{-1}$, m=40.30 mg, n=0.28 mmol) followed by one freeze-pump-thaw cycle. The media was heated at 60° and stirred for 24 h. The polymerisation was stopped by freezing in liquid nitrogen and the media was diluted in THF. The solution was filtered on a silica gel column and the solvent was removed. The polymer was dissolved in THF, precipitated into cold heptane (0°), then solubilized in acetone and precipitated into cold water to give a white solid.

m=1.40 g. yield=31%.

Analytical Data

NMR $^1$H (400 MHz, 25°, CDCl$_3$): 5.16 (q, 1H, O—CH(Me)—CO); 2.20–1.70 (m, 3H, $\underline{CH_2}$—C—P$^t$BuMA backbone); 1.58 (d, 3H, O—CH($\underline{Me}$)—O); 1.42 (m, 6H, C($\underline{Me_3}$)); 1.20–0.70 (m, 4H, $\underline{Me}$-C—P$^t$BuMA backbone).

$^{13}$C (100 MHz, 25°, CDCl$_3$): 177.42 to 176.70(qu)-169.62(qu)-80.91(qu)-80.78(qu)-80.56(qu)-69.02(d)-46.47(qu)-46.23(qu)-27.78(d)-22.69(q)-18.48(q)-17.82(q)-16.64(d).

IR (cm$^{-1}$): 2974(m)-2933(m)-2881(w)-1758(s)-1718(s)-1476(m)-1455(m)-1391(s)-1365(s)-1269(m)-1249(s)-1181(w)-1130(s)-1090(s)-1039(w)-968(w)-941(w)-873(w)-847(s)-752(m).

GPC (THF, standard PS): Mn=1990000 g·mol$^{-1}$, Mw=4970000 g·mol$^{-1}$, Ip=2.50 e) Synthesis of Hydroxypropylcellulose-g-poly-L-lactic acid-b-polymethacrylic Acid (HPC-g-PLLA-b-PMAA) (66% PLLA)

In a round bottom flask, 900 mg of HPC-g-PLLA-b-P$^t$-BuMA were solubilized into 5 ml of dichloromethane. 3 Ml of trifluoroacetic acid were added and the media was stirred at room temperature for 1 h and it became orange. The solvent was removed to give a clear red solid. This one was washed 4 times by diethyl ether to give a red filtrate and a white solid m=0.70 g yield=89%

Analytical Data:

NMR $^1$H (400 MHz, 25°, CDCl$_3$): 3.88 to 3.11 (HPC backbone); 2.00 to 1.89 (m, $\underline{CH_2}$ PMAA backbone); 1.51 to 1.28 (Me PMAA backbone); 1.14 (m, Me HPC).

$^{13}$C (100 MHz, 25°, CDCl$_3$): 182.58(qu)-182.32(qu)-181.38(qu)-171.04(qu)-70.48(d)-58.36(t)-55.91(t)-55.79(t)-46.34(qu)-45.97(qu)-31.18(qu)-28.23(q)-27.77(q)-19.26(q)-17.34(q)-17.08(q)

IR (cm$^{-1}$): 3696 to 2152 (COOH) (m)-2994(m)-2942(m)-2886(w)-1735 (ester) (s)-1696 (COOH) (s)-1479(w)-14501(m)-1383(m)-1368(m)-1264(m)-1157(s)-1132(s)-1084(s)-1042(s)-958(w)-933(w)-865(w)-829(w)-777(w)-756(w)-687(m).

Example 3

Synthesis of a Biodegradable Copolymer Composition According to the Invention—Degree of Substitution of 50% a) Synthesis of Functionalised HPC with Trimethylsilyl Group

A procedure similar to Example 1a) was carried out with the following ingredients 3.3 g of HPC (M=10$^5$ g·mol$^{-1}$, n=3.3.10$^{-5}$ mmol, DP$_n$=150, MU=350.41 g·mol$^{-1}$) 3.97 ml of hexamethyldisilazane (M=161.39 g·mol$^{-1}$, n=18.84 mmol, m=3.04 g, d=0.7742)

50 ml of dried acetonitrile (distilled and stored on molecular sieve)

90=, 5 h m=4.2 g, yield=74%

Analytical Data:

NMR $^1$H (400 MHz, 25°, CDCl$_3$): 5.00–3.00 (m, 5H, HPC backbone); 1.13 (s broad, 3H, $\underline{Me}$ HPC); 0.20 (s, 4.5$\underline{H}$, Si $\underline{Me_3}$).

$^{13}$C (100 MHz, 25°, CDCl$_3$): 102.43(q)-82.90(d)-78.67(q)-74.97(d)-74.74(d)-67.74(d)-67.57(d)-67.63(d)-20.94(d)-17.41(d)-10.36(q)-0.24(d).

IR (cm$^{-1}$): 3470(s)-2965(m)-2927(m)-2891 (m)-2871(m)-1676(s)-1453(s)-1411(s)-1373(m)-1315 (s)-1248(s)-1082 (m)-1007(m)-888(s)-835(s)-747(m)-680(m).

GPC (THF, standard PMMA): M$_n$=44000 g·mol$^{-1}$; M$_n$=280000 g·mol$^{-1}$; Ip=6.34.

b) Synthesis of HPC-g-PLLA (Degree of Substitution: 50% PLLA)

A procedure similar to Example 1b) was carried out with the following ingredients 500 mg of HPC-g-TMS (50% OH group, MU=917.45 g·mol$^{-1}$, n=0.545 mmol)

5.89 g of L-lactide (M=144.13 g·mol$^{-1}$, n=40.87 mmol)

8 ml of dried xylene m=4.72 g, yield=74%.

Analytical Data:

NMR $^1$H (400 MHz, 25°, CDCl$_3$): 5.16 (q, 17H, OC—CH(CH$_3$)—O); 5.0–3.0 (m, 5H, HPC backbone); 4.35 (q, 1H, OC—CH(CH$_3$)—O); 1.58 (d, 51H, OC—CH(CH$_3$)—O); 1.49 (d, 3H, OC—CH(CH$_3$)—O); 1.22 (m, 4.5H, Me HPC); 1.12 (m, 4.5H, Me HPC); 0.14 (s, 4.511, SiMe$_3$).

$^{13}$C (100 MHz, 25°, CDCl$_3$): 169.62(qu)-69.02(d)-66.71(d)-20.52(q)-16.66(q)-16.64(q)-0.15(q).

IR (cm$^{-1}$): 3518(w)-2996(w)-2946(w)-2881(w)-1755(s)-1748(s)-1454(m)-1383(m)-1359(m)-1264(w)-1210(m)-1183(s)-1130(s)-1087(s)-1043(s)-956(w)-920(m)-871(m)-755(m)-695(w).

GPC (THF, standard PS): Mn=371000 g·mol$^{-1}$, Mw=831000 g·mol$^{-1}$, Ip=2.24 c) Synthesis of HPC-g-PLLA-initiator

In a two-necked round bottom flask, 1.30 g of HPC-g-PLLA (MU=7835 g·mol$^{-1}$; n$_{OH}$=0.5 mmol) were solubilized into 10 ml of distilled THF. This solution was cooled down to 0°. Then, 350 μL of Et$_3$N (M=101.19 g·mol$^{-1}$, n=2.49 mmol, m=252 mg, d=0.7255) were added, followed by 261 μL of 2-bromopropionyl bromide (M=215.88 g·mol$^{-1}$, n=2.49 mmol, m=540 mg). The media was stirred at 60° for 72 h to give a suspension. The polymer was obtained by precipitation into water to give a solid, which was solubilized in acetone and precipitated into cold heptane. The solid was dried under vacuum for 24 h.

m=1.27 g. yield=97%.

Analytical Data

NMR $^1$H (400 MHz, CDCl$_3$): 5.18 (q, 10H, Br—CH(Me)—CO—O—CH(Me)—CO); 4.42 (q, 1H, O—CH(Me)—CO—O—CH(Me)Br); 5.09–2.60 (m, 5H, HPC backbone); 1.95 (m, 3H, O—CH(Me)—Br); 1.58 (d, 30H, O—CH(Me)—O); 1.11 (m, Me HPC).

$^{13}$C (100 MHz, CDCl$_3$): 169.62(qu)-69.57(d)-69.02(d)-46.10(t)-39.38(d)-39.29(d)-30.71 (q)-21.60(q)-16.66(q)-8.67(qu).

IR (cm$^{-1}$): 3651(w)-3499(w)-2995(w)-2944(w)-2876(w)-2684(w)-1747(s)-1716(w)-1452(m)-1382(m)-1358(m)-1305(w)-1267(w)-1210(m)-1181 (s)-1128(s)-1082(s)-1042(s)-921 (w)-870(m)-755(m)-686(w).

GPC: (THF, standard PS): Mn=165000 g·mol$^{-1}$, Mw=357000 g·mol$^{-1}$, Ip=2.17 d) Synthesis of poly-L-lactic acid-b-poly-tertio-buthyl-methacrylic Acid (50% PLLA-b-P$^t$BuMA)

In a two-necked round bottom flask of 25 mL, 0.311 g of HPC-g-PLLA-initiator (Mu=3110 g·mol$^{-1}$, n=0.10 mmol) were solubilized in 5.70 ml of distilled anisole. Then, 2.75 ml of tertio-ButylMethacrylate (M=142.20 g·mol$^{-1}$, d=0.875, n=15.00 mmol, DPn=100, m=2.13 g) and 31.3 μl of PMDETA (M=173.30 g·mol$^{-1}$, d=0.83, n=0.15 mmol) were added and followed by two freeze-pump-thaw cycles. Then, the cupper bromide was added (M=143.45 g·mol$^{-1}$, m=21.50 mg, n=0.15 mmol) followed by one freeze-pump-thaw cycle. The media was heated at 60° and stirred for 24 h. The polymerisation was stopped by freezing in liquid nitrogen and the media was diluted in chloroform. The cupper bromide was removed by extraction in water. The polymer was dried on Na$_2$SO$_4$ with a small amount of silica, filtered and then precipitated into cold heptanes (0°) and filtered to give a solid. This one was solubilized in acetone and precipitated into cold water to give a white solid.

m=(0.52 g. yield=29%.

Analytical Data:

NMR $^1$H (400 MHz, 25°, CDCl$_3$): 5.16 (q, 1H, O—CH(Me)—CO); 2.24–1.71 (m, 3H, CH$_2$—C—P$^t$BuMA backbone); 1.58 (d, 3.1H, O—CH(Me)—O); 1.43 (m, 13H, C(Me$_3$)); 1.20–0.70 (m, 4.2H, Me-C—P$^t$BuMA backbone).

IR (cm$^{-1}$): 2974(m)-2931(m)-2881 (w)-2658(w)-1756(s)-1718(s)-1474(m)-1455(m)-1390(m)-1365(s)-1267(m)-1247(s)-1211(m)-1183(s)-1129(s)-1088(s)-1044(s)-968(w)-873(w)-846(s)-752(m)-692(w).

GPC (THF, standard PS): Mn=500000 g·mol$^{-1}$, Mw=1750000 g·mol$^{-1}$, Ip=3.50 c) Synthesis of Poly-L-lactic acid-b-polymethacrylic Acid (50% PLLA-b-PMAA)

In a round bottom flask, 0.45 g of HPC-g-PLLA-b-P$^t$BuMA were solubilized into 5 ml of dichloromethane. 3 Ml of trifluoroacetic acid were added and the media was stirred at room temperature for 1 h. The polymer was obtained by precipitation into cold heptane and filtered to give a white solid.

m=0.30 g; yield=85%

Analytical Data:

NMR $^1$H (400 MHz, 25°, CDCl$_3$): 5.20 (m, 1H, O—CH(Me)—CO); 3.88 to 3.11 (HPC backbone); 2.21 to 1.75 (m, 5H, CH$_2$ PMAA backbone); 1.56 (m, 3.23H, O—CH(Me)—CO); 1.27 to 0.99 (m, 8.1H, Me PMAA backbone).

IR (cm$^{-1}$): 3696 to 2146 (COOH) (m)-2991(m)-2942(m)-2884(w)-1734 (ester) (s)-1696 (COOH) (s)-1481 (m)-1450 (s)-1384(s)-1366(s)-1263(s)-1159(s)-1131 (s)-1085(s)-1044 (s)-961 (m)-933(m)-798(w)-754(w)-690(m).

Example 4

Synthesis of a Biodegradable Copolymer Composition According to the Invention—Degree of Substitution of 33% a) Synthesis of Functionalised HPC with Trimethylsilyl Group

A procedure similar to Example 1a) was carried out with the following ingredients 2 g of HPC (M=10$^5$ g·mol$^{-1}$, n=2.10$^{-5}$ mmol, DP$_n$=150, MU=350.41 g·mol$^{-1}$)

3.61 ml of hexamethyldisilazane (M=161.39 g·mol$^{-1}$, n=17.13 mmol, m=2.76 g, d=0.7742)

30 ml of dried acetonitrile (distilled and stored on molecular sieve)

90°, 24 h m=2.4 g, yield=85%

Analytical Data:

NMR $^1$H (400 MHz, 25°, CDCl$_3$): 5.00–3.00 (m, 5H, HPC backbone); 1.13 (s broad, 3H, Me HPC); 0.20 (s, 6H, SiMe$_3$).

$^{13}$C (100 MHz, 25°, CDCl$_3$): 102.43(q)-84.07(d)-83.09(d)-78.62(q)-75.07(d)-67.81(d)-67.63(d)-67.40(d)-20.99(d)-17.47(q)-1.36(q)-0.29(d).

IR (cm$^{-1}$): 3494(s)-2964(m)-2932(m)-2896(m)-2870(m)-1451(w)-1401(w)-1373(m)-1315(w)-1248(s)-1084(s)-1006(s)-923(s)-888(m)-835(s)-747(s)-684(w).

GPC (THF, standard PMMA): $M_n$=47000 g·mol$^{-1}$; $M_w$=152000 g·mol$^{-1}$; Ip=3.23 b) Synthesis of HPC-g-PLLA (33% PLLA)

A procedure similar to Example 1b) was carried out with the following ingredients 370 mg of HPC-g-TMS (33% OH group, MU=480.80 g·mol$^{-1}$, n=0.77 mmol).

5.55 g of L-lactide (M=1=44.13 g·mol$^{-1}$, n=38.50 mmol).

28 ml of dried xylene.

m=5.06 g, yield=86%.

Analytical Data:

NMR $^1$H (400 MHz, 25°, CDCl$_3$): 5.16 (q, 27H, OC—CH(CH$_3$)—O); 5.0–3.0 (m, 5H, HPC backbone); 4.35 (q, 1H, $\overline{OC}$—CH(CH$_3$)—O) 1.58 (d, 81H, OC—CH(CH$_3$)—O); 1.49 ($\overline{d, 3H}$, OC—CH(CH$_3$)—O); 1.22 (m, 3H, $\overline{Me}$ HPC); 1.12 (m, 6H, Me HPC); $\overline{0.14}$ (s, 3H, SiMC$_3$)—

$^{13}$C (100 $\overline{MHz}$, 25°, CDCl$_3$): 175.$\overline{16}$(qu)-169.62(qu)-69.02(d)-66.71(d)-20.53(q)-16.66(q).

IR (cm$^{-1}$): 3632(w)-3484(w)-2995(w)-2944(w)-2876(w)-1754(s)-1454(m)-1383(m)-1359(m)-1305(w)-1267(w)-1210(m)-1182(s)-1129(s)-1082(s)-1043(s)-955(w)-920(w)-871 (m)-755(m)-693(w).

GPC (THF, standard PS): Mn=536000 g·mol$^{-1}$, Mw=1140000 g·mol$^{-1}$, Ip=2.12 c) Synthesis of HPC-g-PLLA-initiator

In a two-necked round bottom flask, 700 mg of HPC-g-PLLA (MU=1922 g·mol$^{-1}$; $n_{OH}$=0.54 mmol) were solubilized into 7 ml of distilled THF. This solution was cooled down to 0°. Then, 381 μL of Et$_3$N (M=101.19 g·mol$^{-1}$, n=2.73 mmol, m=276 mg, d=0.7255) were added, followed by 286 μL of 2-bromopropionyl bromide (M=215.88 g·mol$^{-1}$, n=2.73 mmol, m=589 mg). The media was stirred at 60° for 72 h to give a suspension. The polymer was obtained by precipitation into water to give a solid, which was solubilized in acetone and precipitated into cold heptane. The solid was dried under vacuum for 24 h.

m=0.65 g. yield=87%.

Analytical Data:

NMR $^1$H (400 MHz, CDCl$_3$): 5.18 (q, 25H, Br—CH(Me)-CO—O—CH(Me)—CO); 4.42 (m, 1H, O—CH(Me)—$\overline{CO}$—O—CH(Me)Br); 5.09–2.60 (m, HPC back$\overline{bone}$); 1.95 (m, 3H, $\overline{OC}$—CH(Me)—Br); 1.58 (d, 75H, O—CH—(Me)—O); 1.11 (m, Me $\overline{HPC}$).

$^{13}$C (100 $\overline{MHz}$, CDCl$_3$): 1$\overline{69}$.62(qu)-69.57(d)-69.44(d)-69.02(d)-39.29(q)-30.33(q)-29.71 (q)-21.60(q)-16.66(q).

IR (cm$^{-1}$): 3504(w)-2993(w)-2944(w)-2876(w)-2643(w)-1747(w)-1451(m)-1381(m)-1358(m)-1305(w)-1264(m)-1209(m)-1181(s)-1128(s)-1085(s)-1042(s)-955(w)-915(w)-867(m)-754(m)-690(w).

GPC: (THF, standard PS): Mn=296000 g·mol$^{-1}$, Mw=889000 g·mol$^{-1}$, Ip=3.00 d) Synthesis of poly-L-lactic acid-b-poly-tertio-butyl Methacrylate (33% PLLA-b-P$^t$BuMA)

In a two-necked round bottom flask of 25 mL, 0.60 g of HPC-g-PLLA-initiator (Mu=3000 g·mol$^{-1}$, n=0.20 mmol) were solubilized in 7.50 ml of distilled THF. Then, 3.40 ml of tertio-ButylMethacrylate (M=142.20 g·mol$^{-1}$, d=0.875, n=20.00 mmol, DPn=100, m=2.84 g) and 42 μl of PMDETA (M=173.30 g·mol$^{-1}$, d=0.83, n=0.20 mmol, m=34.6 mg) were added and followed by two freeze-pump-thaw cycles. Then, the cupper bromide was added (M=143.45 g·mol$^{-1}$, m=28.7 mg, n=0.20 mmol) followed by three freeze-pump-thaw cycles. The media was heated at 60° and stirred for 24 h. The polymerization was stopped by freezing in liquid nitrogen and the media was diluted in chloroform. The cupper bromide was removed by extraction in water. The polymer was dried on Na$_2$SO$_4$ with a small amount of silica, filtered and then precipitated into cold heptane (0°) and filtered to give a solid. This one was solubilized in acetone and precipitated into cold water to give a white solid.

m=1.20 g. yield 35%.

Analytical Data:

NMR $^1$H (400 MHz, 25°, CDCl$_3$): 5.16 (q, 114, O—CH(Me)—CO); 2.26–1.74 (m, 1.5H, CH$_2$—C—P$^t$BuMA $\overline{backbone}$); 1.58 (d, 3.2H, O—CH(Me)—$\overline{O}$); 1.43 (m, 7.30H, C(Me$_3$)); 1.33–0.94 (m, 2.2H, Me-$\overline{C}$—P$^t$BuMA backbone).

$\overline{IR}$ (cm$^{-1}$): 2975(m)-2934(m)-$\overline{2}$876(w)-2648(w)-1754(s)-1718(s)-1601(w)-1475(m)-1454(s)-1390(s)-1365(s)-1247 (s)-1182(s)-1128(s)-1085(s)-1042(s)-968(m)-939(w)-921 (w)-872(m)-846(s)-753(s)-693(w).

GPC (THF, standard PS): Mn=1000000 g·mol$^{-1}$, Mw=1680000 g·mol$^{-1}$, Ip=1.68 e) Synthesis of Poly-L-lactic acid-b-polymethacrylic Acid (33% PLLA-b-PMAA)

In a round bottom flask, 1.00 g of HPC-g-PLLA-b-P$^t$-BuMA were solubilized into 4 ml of dichloromethane. 4 Ml of trifluoroacetic acid were added and the media was stirred at room temperature for 1 h. The polymer was obtained by precipitation into cold heptane and filtered to give a white solid.

m=0.80 g yield=91%

Analytical Data:

NMR $^1$H (400 MHz, 25°, CDCl$_3$): 3.88 to 3.11 (HPC backbone); 2.00 to 1.89 (m, CH$_2$ PMAA backbone); 1.$\overline{51}$ to 1.28 (Me PMAA backbone); $\overline{1.14}$ (m, Me HPC).

$^{13}$C $\overline{(100}$ MHz, 25° C., CDCl$_3$): 18$\overline{2.58}$(qu)-182.32(qu)-181.38(qu)-171.04(qu)-70.48(d)-58.36(t)-55.91 (t)-55.79(t)-46.34(qu)-45.97(qu)-31.18(qu)-28.23(q)-27.77(q)-19.26(q)-17.34(q)-17.08(q)

IR (cm$^{-1}$): 3701 to 2162 (COOH) (m)-2991(m)-2943(m)-2886(w)-1744 (ester) (s)-1698 (COOH) (s)-1434(m)-1451 (s)-1383(s)-1367(s)-1265(m)-1180(s)-1129(s)-1084(s)-1044(s)-959(m)-928(m)-867(w)-829(w)-799(w)-781 (w)-752(w)-688(m).

Example 5

Synthesis of grafted HPC by poly L-lactic acid-b-polyacrylate (HPC-g-PLLA-b-PAA)

In a round bottom flask, acrylate monomers (tertio-butyl acrylate (5d-e), 2-(N,N-dimethylamino)ethyl acrylate (5f), 2-hydroxyethyl acrylate (5g) and diethyleneglycol methyl ether) acrylate (5h) are polymerised as well as in bulk or in dioxane (50% v/v).

Polymers, described in examples 1c, 3c and 4c, are used as initiators. HEMTETA, bipyridine and tris(dimethylamino ethyl)amine are used as ligands and CuBr as catalyst. Polymerisations have been carried out at temperature comprised between 50° C. and 110° C., under nitrogen. Further chemical modifications have been carried out on the poly(tert-butyl acrylate) and the poly(2-(N,N-dimethylamino)ethyl acrylate), corresponding to examples 2e, 3e, 4e and 1e, respectively, to provide HPC-g-PLLA-b-PAA.

Example 6

Preparation of a Fragrance Delivery System with a Copolymer Composition of the Invention A copolymer HPC-g-PLLA-PTMAEMA prepared as described in Example 1 was dried and mixed directly with linalool at the mixing ratio of 50/50% (w/w). The same preparation was done with HPC. The two samples were kept at room temperature for at least one day. Then, an amount of 10 mg of each sample was analysed with Thermogravimetry Analyser by recording the isotherms at 25° under a constant flow of nitrogen gas (20 ml/min). The analysis was repeated three times with HPC-PLLA-PTMAEMA/linalool sample (masse: 8.99, 9.57 and 8.85 mg) and two times with HPC/linalool sample (masse: 9.76 and 9.77 mg). The time of the isotherm was fixed at 200 min.

Example 7

Preparation of a Eau de Toilette (EDT) Comprising the Copolymers of the Invention to Control Release of Fragrances Different copolymers (Examples 1d, 5f and 5g) (0.5 wt. %) have been solubilised in an EDT, containing 80% of ethanol, 10% of water and 10% of a fragrance (benzyle salycilate 35 g, habanolide (1-OXA-12-CYCLOHEXADECEN-2-ONE) 2 g, cetalox 2 g, hedione ((+−)-METHYL 3-OXO-2-PENTYL-1-CYCLOPENTANEACETATE) 35 g, bacdanol (2-ETHYL-4-(2,2,3-TRIMETHYL-3-CYCLOPENTEN-1-YL)-2-BUTEN-1-OL) 1 g, lilial (3-(4-TERT-BUTYLPHE-NYL)-2-METHYLPROPANAL) 10 g, coumarine 1 g, vanillin 2 g, anthranilate (2-AMINOBENZOATE) 1 g, neoflorol ((+−)-TETRAHYDRO-2-ISOBUTYL-4-METHYL-4(2H)-PYRANOL) 1.5 g, styrallyl acetate (1-PHENYLETHYL ACETATE) 1.5 g, benzyle acetate 6 g, zestover (2,4-DIM-ETHYL-3-CYCLOHEXENE-1-CARBALDEHYDE) 2 g).

Then, 10 µL of these solutions are put in an alumina crucible. The weight loss of fragrance has been measured by thermogravimetric analyses (two times each sample) under a constant flow of nitrogen (20 ml/min). The measurements (FIG. 2) start at 25° C. to 50° C. (5° C./min), stay at 50° C. for 115 minutes and then until 150° C. (10° C./min).

The results are shown in FIG. 2. It can be seen that weight loss during 115 minutes at 50° C. is highest with the EDT devoid of the copolymer of the invention (lowest line, "Perfume, EtOH/Eau"), while samples provided with the copolymer of Examples 1d, 5g and 5f of the invention show clearly less loss (upper 3 lines), with small differences between the various polymers.

What is claimed is:

1. A copolymer comprising a polysaccharide backbone and amphiphilic diblock copolymers grafted on the polysaccharide backbone, each amphiphilic diblock comprising:
    a) a hydrophobic polymeric segment directly grafted on the polysaccharide backbone and comprising from 5 to 200 repeated units; and
    b) a hydrophilic polymeric segment covalently bonded to the hydrophobic segment and comprising from 5 to 300 repeated units,
        wherein the amphiphilic diblock copolymers are grafted on the polysaccharide backbone with a degree of substitution via hydroxyl functions such that an average of 30 to 80% of the hydroxyl groups in each saccharide unit are substituted by the diblock copolymer.

2. The polymer according to claim 1, wherein the polysaccharide has a weight average molecular weight higher than 800 g/mol.

3. A polymer according to claim 1, wherein the polysaccharide backbone is selected from the group consisting of dextrans, arabinogalactan, pullulan, cellulose, cellobiose, inulin, chitosan, alginates, hyaluronic acid and cyclodextrins.

4. A polymer according to claim 1, wherein the hydrophobic polymeric segment is selected from the group consisting of polylactides, polycaprolactone, polypropylene glycol and polyanhydrides.

5. A polymer according to claim 1, wherein the hydrophilic polymeric segment is selected from the group consisting of poly(meth)acrylic acid, polydimethyl aminoethyl(meth)acrylate, polytrimethyl ammonium ethyl(meth)acrylate salts, polyhydroxyethyl(meth)acrylate, polymethylether diethyleneglycol(meth)acrylate, polyethylene oxide, polyvinylpyrrolidone, polyaminoacids and polyacrylonitriles.

6. A process for the preparation of a copolymer as defined in claim 1, comprising the steps of
    a) partially sylilating the hydroxyl functions of a polysaccharide chain with a sylilation agent, the ratio between the polysaccharide hydroxyl functions and the sylilation agent being comprised between 1 and 3 equivalents, to provide a modified polysaccharide;
    b) using the modified polysaccharide obtained under a) to polymerise biodegradable hydrophobic monomers by ring opening polymerisation, at a temperature comprised between 120° C. and 150° C. in the presence of a catalyst, to provide a polysaccharide backbone grafted with primary hydrophobic segments;
    c) preparing a macro-initiator by esterification of ending groups of the primary hydrophobic segments with an alkyl bromide used in excess;
    d) using the macro-initiator obtained under c) to polymerise monomers to covalently link secondary segments to the primary segments, thus producing a copolymer diblock composition; and
    e) optionally chemically modifying the secondary segments.

7. A process according to claim 6, wherein the monomers used in step d) are hydrophilic, and in that step e) is not carried out.

8. A process according to claim 6, wherein the monomers used in step d) are hydrophobic, and in that step e) is carried out.

9. A biodegradable particle having a core-shell structure, wherein the particle is made of a copolymer composition according to claim 1.

10. A perfumed product comprising the polymer according to claim 1.

11. A perfumed product according to claim 10, wherein the perfumed product is a perfume, an eau de toilette, a shampoo, a conditioner, a shower gel, a liquid or solid soap, a cream, a lotion, a liquid detergent, a solid detergent, or a fabric softener.

* * * * *